United States Patent [19]

Attenburrow

[11] 4,218,584

[45] Aug. 19, 1980

[54] STETHOSCOPE FOR USE ON A HORSE

[76] Inventor: Donald P. Attenburrow, Langford Farm, Newton St. Cyres, Nr. Exeter, Devon, England

[21] Appl. No.: 950,053

[22] Filed: Oct. 10, 1978

[30] Foreign Application Priority Data

Oct. 10, 1977 [GB] United Kingdom ............... 42118/77

[51] Int. Cl.² .......................... A61B 7/04; H04R 1/46
[52] U.S. Cl. ..................................... 179/1 ST; 119/29
[58] Field of Search .................. 179/1 ST, 121 C, 157; 128/2.05 S, 2.1 A, 2 K; 325/118; 119/29, 101; 54/35, 67, 71

[56] References Cited

U.S. PATENT DOCUMENTS

| | | | |
|---|---|---|---|
| 2,583,941 | 1/1952 | Gordon | 128/2.05 S |
| 2,755,336 | 7/1956 | Zener et al. | 179/1 ST |
| 3,283,181 | 11/1966 | Johanson | 128/2.05 S |
| 3,525,810 | 8/1970 | Adler | 179/1 ST |
| 3,543,724 | 12/1970 | Kirkpatrick et al. | 119/29 |
| 3,867,925 | 2/1975 | Ersek | 128/2.05 S |
| 4,008,711 | 2/1977 | Olinger | 179/1 ST |

FOREIGN PATENT DOCUMENTS

| | | | |
|---|---|---|---|
| 379482 | 9/1932 | United Kingdom | 179/1 ST |
| 1219618 | 1/1971 | United Kingdom | 128/2 K |

OTHER PUBLICATIONS

Behavior Research Methods and Instrumentation, Jun. 1977, vol. 9 (3), pp. 243–246, Instrumentation and Techniques, "A Nonobtrusive Heart Rate Telemetry System for Rats", M. Meinrath et al.

Conference: Proceedings of the 12th Annual Rocky Mountain Bioengineering Symposium and the 12th international ISA Biomedical Sciences Instrumentation Symposium, Denver, Colo., USA, Apr. 28-30, 1975, pp. 57-60, "Mortality-Sensing Wildlife Transmitters", A. Kolz.

*Electronics,* Dec. 23, 1960, pp. 54–55, "Radio Transmitter for Remote Heartbeat Measurements", G. A. Harten et al.

*Primary Examiner*—James W. Moffitt
*Attorney, Agent, or Firm*—Oblon, Fisher, Spivak, McClelland & Maier

[57] ABSTRACT

This invention is a stethoscope for use by a veterinary surgeon with a microphone transducer (15) mounted within a casing arranged to be held by a harness against the skin of the animal, with the transducer opening coupled to the skin through an enclosed column of air, and the harness held in position by a grid (33, 34) capable of being attached to the animal's hair. The output from the transducer can be transmitted from the animal by radio.

7 Claims, 6 Drawing Figures

STETHOSCOPE FOR USE ON A HORSE

This invention is a stethoscope developed for the purpose of detecting and recording data from a horse while it is walking, trotting, cantering, jumping and galloping.

According to the invention a stethoscope comprises a transducer, for example a microphone, and means for attaching and locating the transducer against an animal, and preferably comprises also a radio transmitter adapted to be mounted on the animal or its harness, and to receive an input from the transducer.

The acoustic transducer or microphone is conveniently located in a housing specially designed for the purpose of presenting the sound transducer aperture against the skin of the animal, so that the diaphragm of the sound transducer is coupled to the skin of the animal by an enclosed column of air. The housing can comprise enclosing sound-attenuating material, and in one embodiment is supported by a specially designed harness which is comprised of two units, viz. a strap having a pocket in which the transducer contained in an outer housing can be held secure, and a perforated grid structure which is attached to the strap by two buckles. When in situ on the animal, the hairs on the mane are pulled through the perforations of the grid structure. That part of the transducer housing which is presented to the skin of the animal conveniently carries a disposable pad with adhesive on opposed faces.

The combination of the design of the (a) transducer housings - both inner and outer; (b) the method of suspension of an inner transducer housing in an outer transducer housing; (c) the adhesive disposable pad; (d) slack electrical connections from the transducer to an output; and (e) the strap and grid, enables the sound transducer to be held against the skin of the animal with substantially no relative movement between it and the skin during walking, trotting, cantering, jumping and galloping. Respiratory sounds are detected, and can be remotely recorded by radio link to the exclusion of most or all other ambient sounds.

The invention may be carried into practice in various ways, and one embodiment will now be described by way of example with reference to the accompanying drawings, of which FIG. 1 is a sketch showing the stethoscope mounted around the neck of a horse;

Figure 5:
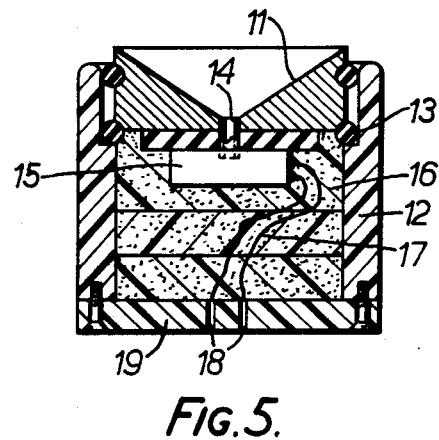
FIG. 5 is a sectional elevation to an increased scale of the transducer shown in outline in FIG. 2.
Figure 6:
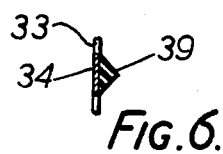
FIG. 6 is a detailed section of the line VI—VI in FIG. 4.

As shown in FIG. 5, the transducer comprises a microphone with an aluminum cone 11 suspended within a perspex cylindrical housing 12 through two annular rubber ring bearings 13 spaced apart axially in a recess in one end of the housing 12. A tube 14 from the apex of the cone 11 leads sound to a conventional acoustic/electric transducer 15 which is embedded within the housing 12 in multi-layer acoustic insulation, shown generally at 16. The electrical output from the transducer 15 is led over slack conductors 17 to a two-pin socket 18 in an end wall 19 of the housing 12.

Figure 1:
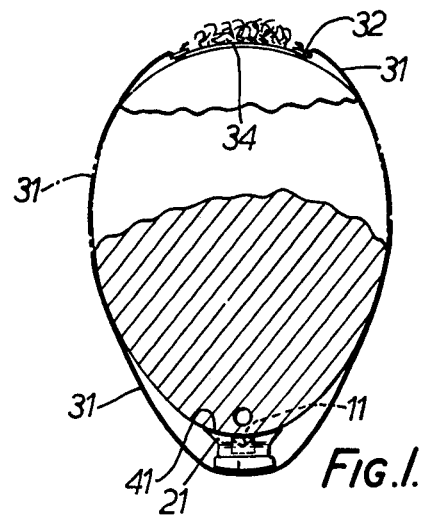
Figure 2:
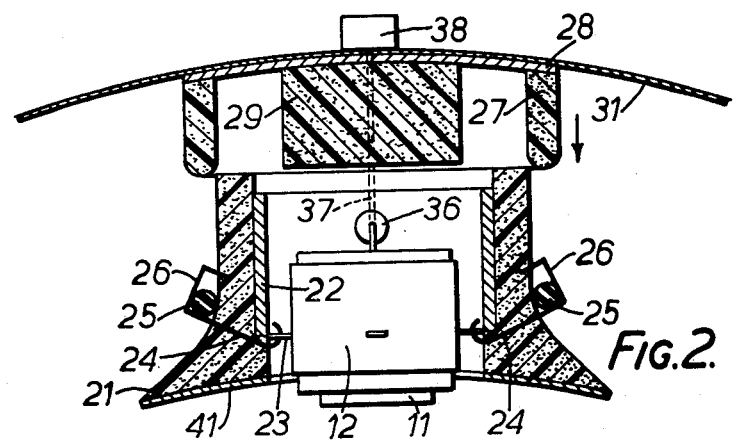
FIG. 2 is a sectional elevation on the line II—ii in FIG. 3 of the transducer of the stethoscope shown in FIG. 1.
Figure 3:
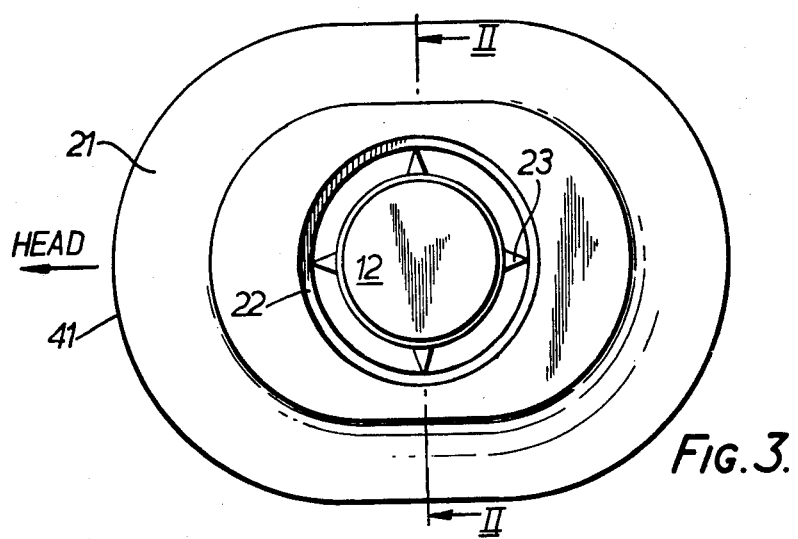
FIG. 3 is an inside view of the transducer and casing shown in FIG. 2 to a reduced scale.

FIG. 2 shows how the microphone of FIG. 5 is suspended within an annular casing 21 so that the entry to the cone 11 can protrude a little from the exposed end of the casing 21 to be in contact with the hide of an animal. The transducer housing 12 is mounted within an aluminium tube 22 inside the casing 21 by a four point suspension, each point of which consists of an external lug 23 on the transducer housing engaged in a stainless steel suspension hook 24 embedded in the casing 21, and stressed radially outwardly by a rubber cord 25 around the outside of the casing 21, and within outward loops 26 on each hook.

The casing 21 is of a shock absorbing and sound-attenuating composite material known as Rubizote and the inner end is a push fit in a Rubizote sleeve 27 extending annularly around the rim of an aluminium back plate 28 whose shape is approximately that of an elongate oval. The back plate 28 carries a central Rubizote pad 29 against which the inner end of the transducer housing 12 can sit snugly when the casing 21 is pushed into the ring 27. The plate 28, and sleeve 17 comprise a pocket holding the transducer in the casing 21.

Figure 4:
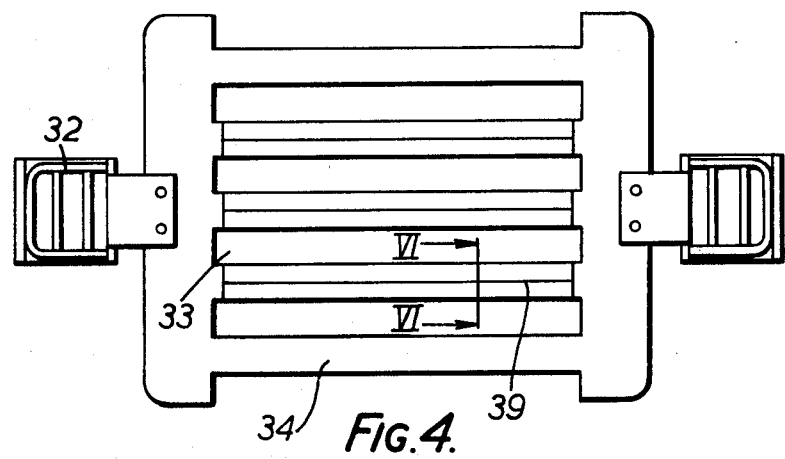
FIG. 4 is a plan view of a harness grid as shown in FIG. 1.

The back plate 28 is secured to the inner side of a strap 31 for fixing around the neck or trunk of the animal whose breathing is to be monitored by means of an adhesive, or of a pocket (not shown) integral with the strap. The transducer housing and casing are held against the hide of the horse adjacent the wind pipe, and the back plate 28 and a pad 41 on the inner face of the casing 21 are curved to correspond with the curvature of the horse's neck. The pad has adhesive on both faces to prevent the casing from slipping around the neck. The strap 31 is controlled against slipping along the neck partly by the pad 41 and partly by a harness grid shown in FIG. 4 having a pair of buckles enabling it to be secured to the strap 31 and consisting of a short length of strap made from multiple laminations of rubberised line, and consisting of an array of elongate apertures 33 separated by bars 34 of strapping, carrying strips 39 of rubber of wedge-shaped cross-section.

The grid is positioned at the horse's mane, and hair from the mane is wound around the grid bars 34 to hold the complete assembly approximately in place.

The assembly measures only about 2 or 3 inches in each direction, and so is quite compact and can be held securely in position without causing the animal any discomfort.

The electrical output from the transducer socket 18 is connected to a coaxial plug 36 embedded in the casing 21, and a coaxial lead 37 extends to a battery powered compact amplifier and radio transmitter 38 which can be fastened at any convenient place to the animal, or preferably to its saddle for radio transmission of the transducer signals after amplification by way of a simple aerial comprising a short length of flexible conductor. A battery powered transmitter with such an aerial can transmit good signals over perhaps a hundred yards or more so that the breathing can be monitored at a distance, for example in a laboratory or in field.

The suspension of the transducer in a sound-attenuating casing, with the only exposed face against the windpipe and the use of slack conductors from the transducer to the plug 36, and a coaxial line 37, makes the unit as free as possible from unwanted noise. The method of locating the microphone in position reduces the likelihood of noise due to rubbing over the horse's hide.

What is claimed as new and desired to be secured by letters patent of the United States is:

1. A stethoscope for use on a horse, comprising a casing, a transducer in said casing, and a harness adapted for attaching to an animal having a mane, said harness including a strap having a pocket in which said transducer and its casing is held, and including a perforated grid structure attached to said strap, said perforated grid structure adapted for being intertwined with the mane of said horse, the pocket being displaced from the grid structure so that said transducer is held against the windpipe of said horse when said grid structure is intertwined with said mane.

2. The stethoscope of claim 1 wherein said perforated grid structure comprises a plurality of bars separated by elongate apertures, said bars including elongate wedge shaped strips of resilient material, wherein said mane is intertwined through said apertures and around said bars, and is held by said bars and said strips.

3. A stethoscope as claimed in claim 1 comprising a radio transmitter for mounting on one of the animal and harness, and connected to receive an input from the transducer.

4. A stethoscope as claimed in claim 1 in which the transducer is in a housing having sound attentuating material encasing the transducer.

5. A stethoscope as claimed in claim 4 including slack electrical conductors from the transducer to an outlet connection, the conductors being embedded in the attentuating material.

6. A stethoscope as claimed in claim 4 in which the housing is resiliently mounted within the casing so that when the casing is located against the animal a transducer aperture is against the skin of the animal whereby the transducer is coupled to the skin of the animal by an enclosed column of air.

7. A stethoscope as claimed in claim 4 including a pad with adhesive on opposed faced on that part of the casing to be presented to the skin of the animal.

* * * * *